United States Patent [19]

Lacefield et al.

[11] Patent Number: 4,658,061

[45] Date of Patent: Apr. 14, 1987

[54] 9-AMINOALKYLFLUORENES

[75] Inventors: William B. Lacefield, Indianapolis; Richard L. Simon, Greenwood, both of Ind.

[73] Assignee: Eli Lilly and Company, Indianapolis, Ind.

[21] Appl. No.: 685,924

[22] Filed: Dec. 24, 1984

[51] Int. Cl.⁴ .................................... C07C 103/22
[52] U.S. Cl. ................................ 564/180; 564/164; 564/169; 544/154; 544/380; 546/203; 546/204; 548/328

[58] Field of Search ............... 564/180, 164, 169, 319, 564/320; 558/427; 560/37, 36; 562/442, 441; 568/326; 544/380, 154; 546/203, 204; 548/528; 514/617, 624, 613

[56] References Cited

U.S. PATENT DOCUMENTS

| | | | |
|---|---|---|---|
| 3,660,485 | 5/1972 | Cusic et al. | 546/203 |
| 3,843,657 | 10/1974 | Lowrie | 564/164 |
| 4,277,495 | 7/1981 | Lacefield et al. | 514/538 |
| 4,382,093 | 5/1983 | Lacefield et al. | 514/619 |
| 4,452,745 | 6/1984 | Lacefield | 260/465 E |
| 4,486,592 | 12/1984 | Lacefield et al. | 564/180 |
| 4,552,982 | 11/1985 | Lacefield et al. | 564/164 |

FOREIGN PATENT DOCUMENTS 1345419  10/1963  France.................................. 546/203

*Primary Examiner*—Paul F. Shaver
*Attorney, Agent, or Firm*—Charles W. Ashbrook; Leroy Whitaker

[57] ABSTRACT

Fluorenes bearing a 9-aminoalkyl substituent are useful antiarrhythmic agents. Pharmaceutical formulations containing such compounds are provided, as well as a method of treatment.

15 Claims, No Drawings

9-AMINOALKYLFLUORENES

BACKGROUND OF THE INVENTION

U.S. Pat. No. 4,452,745 describes a group of 9,9-disubstituted fluorenes that are useful as antiarrhythmic agents. The reference draws particular attention to certain 9-carbamoyl-9-(3-aminopropyl)fluorenes. One compound within this preferred group, namely 9-(3-isopropylaminopropyl)-9-aminocarbonylfluorene, is now known generically as indecainide. Indecainide has shown significant potential as a clinically useful antiarrhymic agent.

The present invention provides certain 9,9-disubstituted fluorenes that are not taught by the prior art. The compounds are potent antiarrhythmic agents.

SUMMARY OF THE INVENTION

This invention provides fluorenes defined by the formula

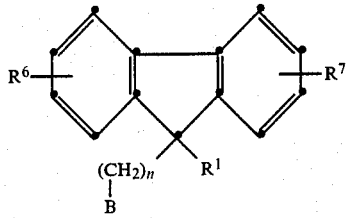

wherein:

$R^1$ is hydroxy, cyano, $COOR^4$, or $CONR^4R^5$ in which $R^4$ and $R^5$ independently are hydrogen or $C_1$–$C_6$ alkyl;

B is

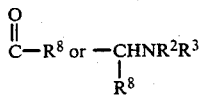

in which $R^2$ and $R^3$ independently are hydrogen, $C_1$–$C_6$ alkyl, $CH_2C_2$–$C_5$ alkenyl, phenyl-$C_1$–$C_3$ alkyl,

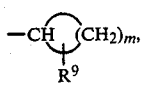

or taken together with the nitrogen to which they are attached, $R^2$ and $R^3$ form a cyclic group of the formula

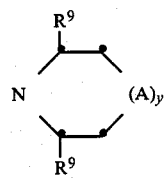

in which $R^8$ and $R^9$ independently are hydrogen or $C_1$–$C_4$ alkyl, m and n independently are 2, 3, 4 or 5, A is $CH_2$, O or NH and y is zero or one;

$R^6$ and $R^7$ independently are hydrogen, $C_1$–$C_4$ alkyl or halogen;

provided that $R^8$ is $C_1$–$C_4$ alkyl when both of $R^2$ and $R^3$ are other than

and the pharmaceutically acceptable salts thereof.

Preferred compounds of the invention have the formula

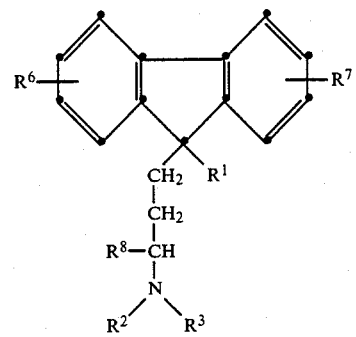

wherein $R^1$, $R^2$, $R^3$, $R^6$, $R^7$ and $R^8$ are as defined above. Especially preferred within this group are the 9-carbamoyl fluorenes wherein $R^1$ is $CONR^4R^5$. Also preferred are the N-cycloalkylaminoalkyl fluorenes wherein one of $R^2$ and $R^3$ is a cycloalkyl group of the formula

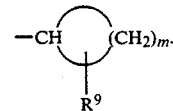

This invention also provides pharmaceutical formulations comprising a compound of the above formula together with a pharmaceutically acceptable carrier or diluent therefor. Also provided is a method for treating cardiac arrhythmias comprising administering an effective amount of a fluorene of this invention.

DETAILED DESCRIPTION OF THE INVENTION

As used herein, the term "$C_1$–$C_6$ alkyl" refers to both straight and branched chain groups such as methyl, ethyl, n-propyl, iso-propyl, n-butyl, iso-butyl, tert-butyl, n-pentyl, iso-pentyl, n-hexyl, 2-methylbutyl, 2-ethylbutyl, and the like. Preferred alkyl groups are $C_1$–$C_3$ alkyl groups such as methyl, ethyl and iso-propyl. "$C_1$–$C_4$ Alkyl" includes groups such as methyl, ethyl, n-butyl, and sec-butyl.

The term "$CH_2C_2$–$C_5$ alkenyl" includes unsaturated carbon chains such as allyl, 2-butenyl, 2-pentenyl, 2-hexenyl, 2-methyl-2-pentenyl, 3-hexenyl, 4-methyl-2-pentenyl, and related alkenyl groups. Typical examples of phenyl-$C_1$–$C_3$ alkyl groups include benzyl, 2-phenethyl and 3-phenylpropyl.

$R^2$ and $R^3$ can be taken together with the nitrogen atom to which they are attached to complete a heterocyclic ring. Examples of such rings include pyrrolidino, piperidino, piperazino, morpholino, 2,6-dimethylpiperidino, 2,6-diethylpiperidino, 2,5-dimethylpyrrolidino, and the like.

$R^2$ and $R^3$ can independently be a cycloalkyl group such as cyclopropyl, cyclobutyl, cyclopentyl, cyclohexyl, 2-methylcyclopropyl, 2-ethylcyclobutyl, 2-isopropylcyclopentyl, 3-n-butylcyclohexyl and the like. Preferred cycloalkyl group are $C_3$–$C_6$ cycloalkyl.

Examples of "halogen" as used herein include fluorine, chlorine, bromine and iodine.

The fluorenes of this invention can be prepared by a variety of methods. One method, for example, for preparing 9-cycloalkylaminoalkyl-9-hydroxyfluorenes of the invention comprises reacting a fluoren-9-one with an aminoalkyne in the presence of a strong base to provide the corresponding 9-aminoalkynyl-9-hydroxyfluorene, which upon hydrogenation affords the corresponding 9-aminoalkyl-9-hydroxylfluorene of the invention. Such process can be illustated as follow, for example where one or both of $R^2$ and $R^3$ are cycloalkyl such as cyclopropyl:

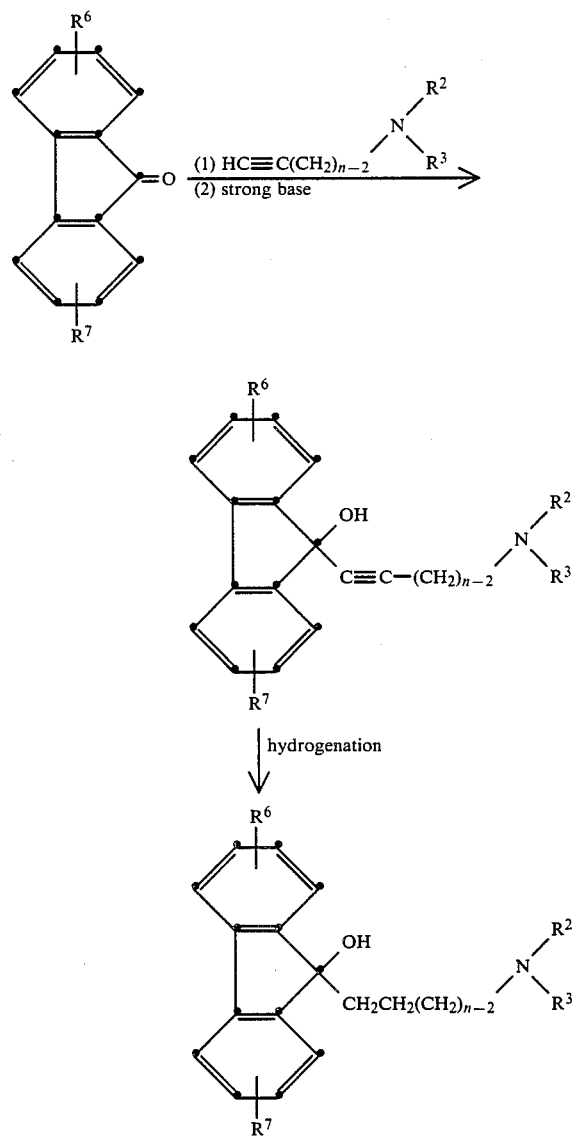

Fluoren-9-ones which can be utilized include fluoren-9-one, 1,8-dimethylfluoren-9-one, 2,7-dibromofluoren-9-one, 3-ethyl-8-n-butylfluoren-9-one, and the like.

The alkynylation of a fluoren-9-one is carried out by combining approximately equimolar amounts of a strong base with an aminoalkyne. Strong bases commonly utilized include alkali metal lower alkyl metalides such as methyl lithium, n-butyl lithium, methyl sodium; alkali metal amides such as sodium amide, potassium amide and lithium diisopropylamide, as well as alkali metal hydrides such as sodium and potassium hydride. Examples of aminoalkynes commonly used include 3-cyclopropylaminopropyne, 4-cyclobutylaminobutyne, 5-isopropylaminopentyne, 3-(N-isopropyl-N-cyclopropylamino)propyne and the like. Typically the strong base and aminoalkyne are combined in an unreactive organic solvent such as diethyl ether, tetrahydrofuran, toluene, 1,2-dimethoxyethane, xylene, or the like, and stirred for about one hour at a reduced temperature of about $-40°$ to about $-80°$ C. The fluoren-9-one is then added to the cold reaction mixture and stirring is continued at sub-zero temperature for about one hour, after which time the mixture is heated to about 30° to 80° C. and stirred for an additional eight to sixteen hours. After the reaction is complete, the mixture is diluted with water, thus decomposing any remaining strong base, and then the product is extracted into a suitable water immiscible solvent such as diethyl ether or ethyl acetate. Removal of such solvent, for instance by evaporation under reduced pressure, provides the corresponding 9-aminoalkynyl-9-hydroxyfluorene. Such intermediate can be further purified if desired by routine methods such as chromatography, distillation, salt formation, or the like.

The 9-aminoalkynyl-9-hydroxyfluorene thus obtained can be converted to the corresponding 9-aminoalkyl-9-hydroxyfluorene of this invention by hydrogenation in the presence of a catalyst such as platinum or palladium on carbon. Such hydrogenation reactions generally are carried out in a solvent such as ethyl acetate or ethanol, and normally are complete after about two to ten hours when carried out at a hydrogen pressure of about 60 psi and at a temperature of about $-25°$ to about 110° C. The product, a 9-aminoalkyl-9-hydroxyfluorene of this invention, can be isolated by simply filtering off the catalyst and removing the reaction solvent, for example by evaporation. The product can be further purified if needed by routine methods such as distillation or salt formation.

The 9-aminoalkyl-9-hydroxyfluorenes can alternatively be prepared by reaction of a fluoren-9-one with an aminoalkyl Grignard reagent. For example, reaction of fluoren-9-one with a Grignard reagent such as 3-cyclopropylaminopropyl magnesium chloride affords, after a standard work-up and isolation, the corresponding 9-aminoalkyl-9-hydroxyfluorene, namely 9-(3-cyclopropylaminopropyl)-9-hydroxyfluorene.

The compounds of this invention wherein $R^1$ is cyano, i.e. the 9-aminoalkyl-9-cyanofluorenes, can be prepared by alkylation of a 9-cyanofluorene with an aminoalkyl alkylating agent. Typical alkylating agents include aminoalkyl halides such as 3-cyclobutylaminopropyl chloride, 3-cyclopropylaminopropyl bromide, and 4-(2-ethylcyclopentyl)amino)butyl iodide. Typical 9-cyanofluorene starting materials include 2-bromo-9-cyanofluorene, 3-n-propyl-9-cyanofluorene, 2,7-difluoro-9-cyanofluorene, and the like.

The alkylation reaction is carried out by commingling approximately equimolar quantities of a 9-cyanofluorene and an aminoalkyl alkylating agent in a suitable unreactive solvent such as toluene or benzene and in the presence of about an equimolar quantity of strong base such as sodium amide, lithium amide, n-butyl lithium, sodium methoxide, potassium tert-butoxide or the like. The alkylation normally is substantially complete after about ten to twenty hours when carried out at a temperature from about 30° to about 150° C. The alkylated fluorene, i.e. the 9-aminoalkyl-9-cyanofluorene, can be isolated by simply diluting the reaction mixture with water and then extracting the product therefrom into a water immiscible solvent such as dichloromethane, diethyl ether or the like. Removal of the solvent then provides the 9-cyanofluorene of this invention, which can be further purified if desired by routine methods, including distillation and salt formation.

The 9-aminoalkyl-9-cyanofluorenes thus prepared are valuable antiarrhythmic agents, and additionally serve as intermediates leading to the acids and primary 9-carboxamides of this invention, i.e. compounds of the above formula wherein $R^1$ is $COOR^4$ or $CONR^4R^5$ and $R^4$ and $R^5$ both are hydrogen. The 9-aminoalkyl-9-cyanofluorenes can be hydrolyzed to the corresponding acids or primary carboxamides by reaction with any of a number of acids such as concentrated sulfuric acid, acetic acid and boron trifluoride, dry hydrogen chloride; or alternatively by reaction with hydrogen peroxide and a base such as sodium hydroxide, or with manganese dioxide in dichloromethane. A preferred hydrolysis process comprises simply heating a solution of the 9-aminoalkyl-9-cyanofluorene in sulfuric acid for about one hour at a temperature of about 90° to 100° C. The corresponding primary carboxamide that is formed is readily isolated by making the reaction mixture alkaline, for example by adding sodium hydroxide until the pH reaches about 10, and then extracting the primary carboxamide into a suitable water immiscible solvent such as diethyl ether or benzene. Evaporation of the organic solvent then provides the desired 9-aminoalkyl-9-aminocarbonylfluorene. Such compound can be further purified if desired by crystallization or salt formation.

Compounds of this invention wherein $R^1$ is $CONR^4R^5$ and one or both of $R^4$ and $R^5$ are alkyl can be prepared by reacting a 9-aminoalkyl-9-fluorenyl caroxylic acid halide or lower alkyl ester with a primary or secondary amine of the formula For example, a fluorenyl carboxylic acid such as 9-(3-N-benzyl-N-cyclopropylaminopropyl)-9-hydroxycarbonylfluorene can be reacted with oxalyl chloride to give the corresponding acid chloride, namely 9-(3-N-benzyl-N-cyclopropylaminopropyl)-9-chlorocarbonylfluorene. Reaction of the latter compound with an amine such as methylamine affords the corresponding methyl substituted carboxamide, namely 9-(3-N-benzyl-N-cyclopropylaminopropyl)-9-methylaminocarbonylfluorene.

The substituted carboxamides of the invention can alternatively be prepared by reacting a substituted amine with an ester of a fluorene 9-carboxylic acid. This method is similar to that described in U.S. Pat. No. 3,660,485. For example, an ester such as 9-(3-cyclobutylaminopropyl)-9-methoxycarbonylfluorene can be reacted with an excess of an amine such as n-propylamine in a suitable solvent such as toluene to provide the corresponding carboxamide, namely 9-(3-cyclobutylaminopropyl)-9-cyclopropylaminocarbonylfluorene.

The compounds comprehended by this invention alternatively can be prepared by first synthesizing a 9-(unsubstituted aminoalkyl)fluorene, and then alkylating such compound with the desired $R^2$ or $R^3$ alkylating agents. Such process is depicted by the following scheme:

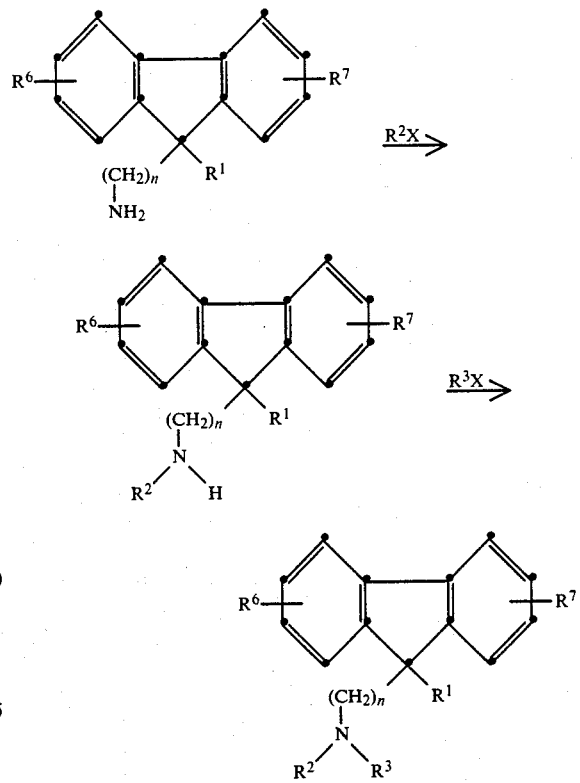

in which n, $R^1$, $R^2$, $R^3$, $R^6$ and $R^7$ have the above-defined meanings, and X is a leaving group such as halogen. Alkylation of primary amines is well known in the art and typically is carried out by combining an amine and an alkylating agent in the presence of a base such as sodium bicarbonate or triethylamine to act as an acid scavenger. The reactions normally are carried out in organic solvents such as toluene, dimethylsulfoxide, ethanol, methanol or the like. As an illustration of the process, a fluorene derivative such as 9-(3-aminopropyl)-9-cyanofluorene can be mixed with about an equimolar quantity of an alkylating agent such as cyclohexyl bromide in a solvent such as benzene and in the presence of triethylamine. The reaction mixture can be heated to about 50° C. and stirred for about two hours to provide the corresponding alkylated aminopropylfluorene derivative wherein $R^2$ is cyclohexyl, namely 9-(3-cyclohexylaminopropyl)-9-cyanofluorene. Further alkylation of such secondary amine with yet a different alkylating agent, for example $R^3X$ wherein $R^3$ is benzyl, affords the corresponding tertiary amine, namely 9-(3-N-cyclohexyl-N-benzylaminopropyl)-9-cyanofluorene. It should be at once recognized that hydrolysis of the cyano moiety as hereinabove discussed provides the corresponding 9-carboxamide derivative.

A similar yet alternative process involves, as a first step, reaction of a fluorene such as a 9-cyanofluorene with a strong base such as sodium amide, and an alkylene dihalide such as 1,3-dichloropropane or 1,5- dibromopentane, to provide the corresponding 9-cyano-9-(ω-haloalkyl)fluorene, which is then condensed with an amine of the formula $HNR^2R^3$ to give a compound of the invention.

Still another method for preparing compounds of the invention comprises reductive amination of a 9-cyanoalkylfluorene by reaction with an amine of the formula $HNR^2R^3$ in the presence of hydrogen and a hydrogenation catalyst. Such method is particularly preferred for the preparation of 9-cyano and 9-aminocarbonylfluorene derivatives which bear an aminopropyl moiety at the 9-position. For example, a 9-substituted fluorene such as 9-aminocarbonylfluorene can be reacted with a cyanoalkene such as acrylonitrile in the presence of a base such as sodium hydride or Triton B to provide the corresponding 9-aminocarbonyl-9-(ω-cyanoalkyl)fluorene, for instance 9-aminocarbonyl-9-(2-cyanoethyl)fluorene. The latter compound can then be reacted with an amine, for instance cyclohexylpropylamine or the like, in the presence of hydrogen and a catalyst such as palladium on carbon. The hydrogenation generally is carried out at a pressure of about 50 to about 2000 psi and at a temperature of about 50° to about 100° C. to provide the 9-aminoalkylfluorene of the invention. Isolation and purification of the product can be accomplished by routine procedures. Simple hydrogenation of a 9-(ω-cyanoalkyl)fluorene in the presence of a solvent such as acetic acid provides the corresponding 9-(ω-unsubstituted aminoalkyl)fluorene.

Various of the compounds provided by this invention are useful as intermediates in addition to being valuable antiarrhythmic agents. For example, the N-benzyl aminoalkylfluorenes of the above formula can be de-benzylated by hydrogenation in the presence of a catalyst such as palladium. Similarly, N-methyl aminoalkylfluorenes can be de-methylated. For example, a compound such as 9-(4-N-cyclopropyl-N-methylaminobutyl)-9-cyanofluorene can be reacted with a haloformate such as phenyl chloroformate to form a carbamate, which when reacted with alkali is hydrolyzed to the corresponding secondary amine, namely 9-(4-N-cyclopropylaminobutyl)-9-cyanofluorene. The latter compound is a potent antiarrhythmic agent, and additionally can be utilized as an intermediate in the preparation of other antiarrhythmic agents. For instance, normal alkylation with an alkylating agent such as 3-phenylpropyl bromide affords 9[4-N-(3-phenylpropyl)-N-cyclopropylaminobutyl]-9-cyanofluorene.

The compounds of the above formula wherein $R^8$ is $C_1$–$C_4$ alkyl are preferably prepared by reductive amination of an oxoalkylfluorene, for example compounds wherein B is

The latter compounds are prepared by reacting a 9-substituted fluorene (e.g. $R^1$ is cyano or carboxamide) with an alkyl vinyl ketone in the presence of a base. This overall reaction scheme is depicted as follows:

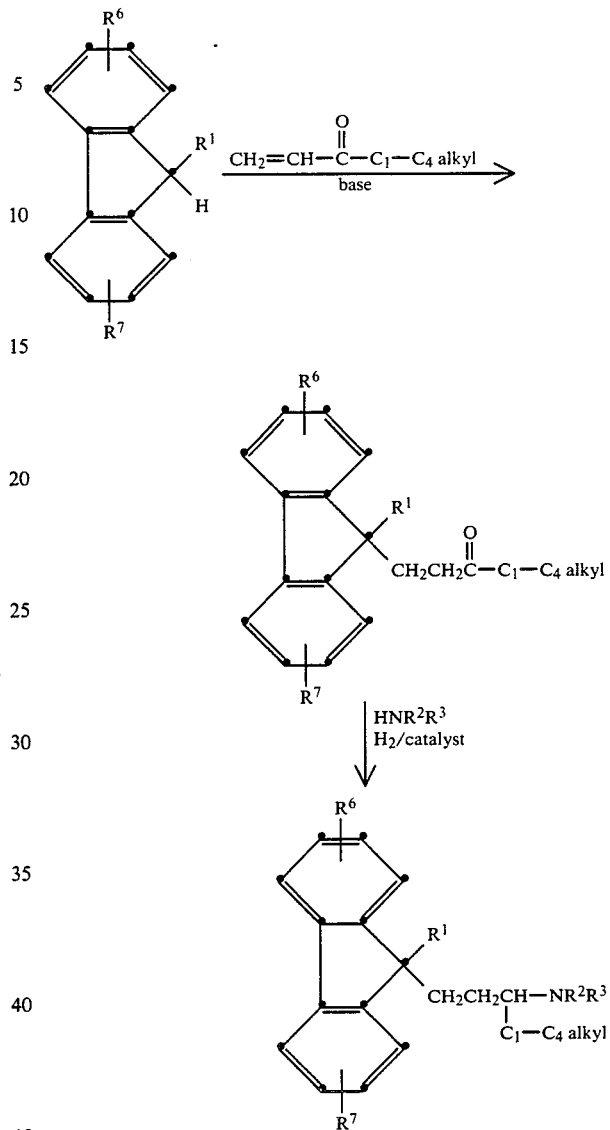

Another method for preparing the branched alkyl compounds wherein $R^8$ is $C_1$–$C_4$ alkyl comprises reacting a 9-substituted fluorene such as 9-cyanofluorene with an amino alkyl halide of the formula

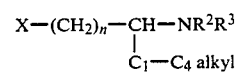

where X is halo such as chloro or iodo. The reaction is carried out in the presence of a strong base such as sodium amide or the like, and generally is substantially complete after about two to twenty hours when conducted at about 0° to about 100° C.

The compounds provided by this invention are basic in nature by virtue of the nitrogen atom of the 9-aminoalkyl substituent. Such compounds consequently react with a number of acids to form salts. This invention additionaly provides pharmaceutically acceptable acid addition salts of the compounds defined by the above general formula, which are those acid addition salts which add no substantial toxicity to the free base from which they are derived. The pharmaceutically acceptable acid addition salts thus provided are prepared by reacting a 9-aminoalkylfluorene of this invention with any of a number of acids. Inorganic acids commonly utilized include hydrochloric, hydrobromic, phosphoric, sulfuric, nitric, perchloric and similar acids. Organic acids frequently utilized to form pharmaceutically acceptable acid addition salts include acetic, succinic, maleic, methanesulfonic, citric, fumaric, para-toluenesulfonic, and related organic acids.

Additionally provided herein are the lower alkyl quaternary ammonium salts which can be prepared when $R^2$ and $R^3$ in the above general formula both are other than hydrogen. For example, normal alkylation of a tertiary amine such as 9-(3-N-methyl-N-cyclopropylaminopropyl)-9-aminocarbonylfluorene by reaction with a lower $C_1$–$C_6$ alkylating agent such as methyl chloride, ethyl bromide, n-butyl iodide, isohexyl bromide, or the like, affords the corresponding quaternary ammonium salt. Such salts characteristically are highly crystalline solids and can be purified by recrystallization from solvents such as ethanol, water, and the like.

The following compounds are representative of those comprehended by this invention.

9-(4-methylaminopentyl)-9-hydroxyfluorene;
9-(3-cyclopropylaminopropyl)-9-hydroxyfluorene;
9-(3-isopropylaminobutyl)-9-hydroxyfluorene;
9-(3-cyclohexylaminopropyl)-9-hydroxy-3,7-diethylfluorene;
9-(3-tert-butylaminobutyl)-9-hydroxy-5-bromofluorene hydrobromide;
9-(4-allylaminopentyl)-9-hydroxyfluorene;
9-[3-(2-butenylamino)butyl]-9-hydroxyfluorene;
9-[3-(2-phenylethylamino)butyl]-9-hydroxy-3-iodofluorene;
9-(3-ethylaminohexyl)-9-cyanofluorene;
9-(3-isopropylaminopentyl)-9-cyanofluorene;
9-(3-cyclopropylaminopropyl)-9-cyanofluorene;
9-(3-benzylaminoheptyl)-9-cyanofluorene;
9-(3-allylaminobutyl)-9-cyanofluorene;
9-[4-(3-phenylpropylamino)pentyl]-9-cyano-2,7-dichlorofluorene;

9-(4-N-isopropyl--N-cyclopentylaminobutyl)-9-cyanofluorene;
9-(3-N,N-dicyclopropylaminopropyl)-9-cyano-1,8-dimethylfluorene;
9-[3-N-cyclopropyl-N-(2-phenylethyl)aminopropyl]-9-cyanofluorene;
9-[3-(3-hexenylamino)hexyl]-9-cyanofluorene;
9-(3-diethylaminobutyl)-9-cyanofluorene;
9-(3-cyclopropylaminopropyl)-9-cyanofluorene hydrosulfate;
9-(4-dibenzylaminohexyl)-9-cyanofluorene ethyl iodide;
9-(3-n-propylaminopentyl)-9-aminocarbonyl-3-ethylfluorene;
9-(3-benzylaminobutyl)-9-aminocarbonylfluorene;
9-(3-cyclopentylaminopropyl)-9-aminocarbonyl-4-bromofluorene;
9-(3-cyclopropylaminopropyl)-9-aminocarbonylfluorene hydrophosphate;
9-(3-N-methyl-N-cyclobutylaminopropyl)-9-aminocarbonylfluorene;
9-[3-(2-hexenylamino)butyl]-9-aminocarbonylfluorene
9-[3-N-(2-phenylethyl)-N-isobutylaminobutyl]9-aminocarbonylfluorene;
9-(3-N,N-di-n-hexylaminopentyl)-9-aminocarbonylfluorene;
9-[3-N-(2-methylcyclopentyl)-N-ethylaminopropyl]-9-aminocarbonylfluorene;
9-(3-N-benzyl-N-cyclobutylaminopropyl)-9-aminocarbonylfluorene n-propyl iodide;
9-(3-cyclopropylaminopropyl)-9-aminocarbonylfluorene hydroacetate;
9-(3-cyclopropylaminopropyl)-9-methylaminocarbonylfluorene;
9-(3-diethylaminobutyl)-9-dimethylaminocarbonylfluorene;
9-(3-tert-butylaminopentyl)-9-isopropylaminocarbonylfluorene;
9-(3-cyclopropylaminopropyl)-9-isopropylaminocarbonylfluorene hydrochloride;
9-(3-benzylaminobutyl)-9-di-n-butylaminocarbonylfluorene;
9-(4-allylaminoheptyl)-9-n-hexylaminocarbonylfluorene;
9-(3-morpholinobutyl)-9-aminocarbonylfluorene;
9-(3-pyrrolidinopentyl)-9-aminocarbonylfluorene;
9-(3-piperidinohexyl)-9-cyanofluorene;
9-(4-piperazinoheptyl)-9-ethylaminocarbonylfluorene;
9-(3-aminobutyl)-9-isopropylaminocarbonylfluorene;
9-(3-diisopropylaminobutyl)-9-diisopropylaminocarbonylfluorene methiodide; and
9-[3-N-(2-butenyl)-N-(2-methylcyclobutyl)aminobutyl]-9-aminocarbonylfluorene.

The 9-aminoalkylfluorenes provided by this invention are useful as antiarrhythmic agents. Such utility has been determined by evaluating representative compounds of the invention in biological assays designed to measure antiarrhythmic activity. One such assay comprises administering a compound of unknown biological activity to a dog suffering from an experimentally induced cardiac arrhythmia, and observing whether or not the compound effects a conversion of the arrhythmia to a normal sinus rhythm, and if so, for how long the conversion persists.

In a typical experiment to determine the activity of the compounds of this invention, one or more mongrel dogs of either sex were anesthetized with sodium pentobarbital. A 23 gauge Butterfly infusion needle was placed in the radial vein for the introduction into the dog of sufficient ouabain to induce an arrhytmia, and for the introduction into the dog of the test compound. Each dog was continuously monitored throughout the experiment by electrocardiogram. After the ouabain induced cardiac arrhythmia had continued for thirty minutes, a compound of this invention was administered via the Butterfly infusion needle at the rate of 200 µg per kilogram of dog body weight per minute. If the arrhythmia was not converted to a normal sinus rhythm within ten minutes from the initial administration of test compound, as observed by electrocardiogram, the rate of infusion of test compound was increased to 500 µg per kilogram per minute. The amount of test compound required to convert an arrhythmia to normal rhythm was recorded as the "converting dose". Following the complete administration of test compound to the dog, the dog's heart was monitored by electrocardiogram until such time that an arrhythmia returned to the dog's heart, or for a maximum time of two hours, at which time the experiment was terminated. The duration of normal rhythm was recorded in minutes.

The results of several experiments are set out in the following table. The average converting dose is given in mg. per kilogram of animal body weight. Average duration of conversion is recorded in minutes.

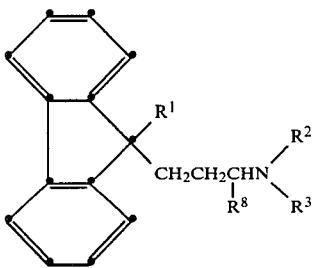

| R¹ | R² | R³ | R⁸ | Converting dose mg/kg | Duration minutes |
|---|---|---|---|---|---|
| CONH₂ | H | CH₃ | CH₃ | 0.8 | 120+ |
| CONH₂ | CH₃ | CH₃ | CH₃ | 1.0 | 120+ |
| CONH₂ | H | CH₂CH₃ | CH₃ | 1.1 | 120+ |
| CONH₂ | H | ◁ | H | 0.8 | 120+ |
| CONH₂ | CH₃ | CH(CH₃)CH₃ | CH₃ | 2 | distinct conversion not observed; strong depression of sinus rhythm observed in two dogs. |

The compounds of this invention can be employed in combatting cardiac arrhythmias in animals by administering an antiarrhythmic amount of one or more of the aminoalkylfluorenes to an animal. The compounds are effective as antiarrhythmic agents when administered internally to an animal so as to introduce the compound into the animal's cardiovascular system. Parenteral administration of the compounds can be accomplished by intraperitoneal, subcutaneous or intravenous injection. The compounds alternatively can be administered orally in the form of tablets, capsules, elixirs, syrups, buccal seals and the like. The aminoalkylfluorenes of this invention have good antiarrhythmic activity both therapeutically, for instance when administered to an animal suffereing from an arrhythmia and in need of treatment, and prophylactically when administered to an animal suspected of developing an arrhythmia, thereby protecting the animal against the occurrence or recurrence of arrhythmias.

The compounds provided herein are preferably utilized in the form of pharmaceutical formulations. The invention therefore provides as another embodiment pharmaceutical formulations comprising a suitable pharmaceutical carrier, diluent, or excipient admixed with a fluorene antiarrhythmic agent of the invention.

Preferred pharmaceutical formulations employ a compound of the above formula wherein $R^1$ is hydroxy, cyano or $CONR^4R^5$, n is 2, $R^2$ is hydrogen, $R^3$ is alkyl or cycloalkyl, $R^6$ and $R^7$ both are hydrogen, and $R^8$ is hydrogen, methyl or ethyl.

The formulations provided herein ideally contain from about 1 to about 50 percent by weight of an aminoalkylfluorene in combination with a suitable diluent, excipient or carrier therefor. Diluents commonly utilized in formulating the compounds in solid form suitable for oral administration include starch, lactose, gelatin, silica gel, rice flour, carboxymethyl cellulose and the like. Carriers employed in liquid formulations suitable for parenteral administration via the intravenous, intramuscular, or subcutaneous routes include water, saline, glucose syrup, ethanol, corn oil and the like.

The 9-aminoalkylfluorenes of this invention can be administered to a subject suffering from an arrhythmia and in need of treatment, or to a subject suspected of developing an arrhythmia and in need of prophylactic treatment. Parenteral administration may be preferred for subjects suffering from a life threatening arrhythmia. Oral administration generally is preferred for maintenance or prophlylactic treatment. The compounds ideally are formulated in such a way that the effective dose of 9-aminoalkylfluorene is an amount sufficient to treat the arrhythmia. Such doses typically will be from about 0.05 to about 25 mg./kg. A typical oral dose for the treatment of a patient suffering from an arrhythmia will be, for example, from about 3.5 to about 400 mg., preferably from about 1.0 to about 200 mg., of a suitably formulated aminoalkylfluorene, for instance 9-(3-cyclopropylaminopropyl)-9-aminocarbonylfluorene, preferably as a pharmaceutically acceptable acid addition salt such as the hydrochloride salt. Such oral dosing may be made from 1 to about 4 times each day, or as dictated by the particular patient and condition being treated. Such compound can of course be formulated for parenteral administration, for instance by intravenous infusion. Such formulation can be prepared by dissolving about 500 mg. of the above-noted compound in a suitable diluent such as 1000 ml. of 5 percent glucose. Such solution can be infused at the rate of about 1 ml. per minute into a patient suffering from an arrhythmia.

The preparation of the aminoalkylfluorenes of this invention is more fully described in the following detailed examples. It is to be understood, however, that the examples are illustrative of the compounds embraced by this invention and are not to be construed as limiting the invention to the particular compounds or methods specifically described.

EXAMPLE 1

9-Carbamoyl-9-(3-cyclopropylaminopropyl)fluorene

A solution of 4.6 g. of 9-carbamoyl-9-(2-cyanoethyl)-fluorene in 200 ml. of ethanol containing 2.3 g. of 5% palladium on carbon and 10.0 g. of cyclopropylamine was stirred under hydrogen at 60 psi at 90° C. for sixteen hours. The reaction mixture was cooled to 25° C., filtered and concentrated to a volume of 20 ml. The oil was dissolved in 200 ml. of 50% ethyl acetate-diethyl ether and the solution was extracted with 6N hydrochloric acid. The acid layer was cooled and made alkaline by addition of 10% aqueous sodium hydroxide. The alkaline solution was extracted several times with fresh diethyl ether-ethyl acetate. The organic extracts were combined, washed with water, dried and the solvent was removed by evaporation to give 3.7 g. of the title comound as an oil. The oil was diluted by addition of 1.4 g. of maleic acid and the mixture was further diluted by addition of 50 ml. of ethyl acetate. The precipitated crystals were collected by filtration and dried to afford 1.5 g. of 9-carbamoyl-9-(3-cyclopropylaminopropyl)-fluorene maleate. m.p. 163°–165° C.

Analysis calc. for $C_{24}H_{26}N_2O_5$; Theory: C, 68.23; H, 6.20; N, 6.63. Found: C, 68.14; H, 6.35; N, 6.54.

EXAMPLE 2

9-Carbamoyl-9-(3-oxobutyl)fluorene

To a stirred warm (45° C.) solution of 62.7 g. (0.3 mole) of 9-carbamoylfluorene in 700 ml. of tetrahydrofuran were added in one portion 30 ml. of a 40% aqueous solution of benzyltrimethylammonium hydroxide. The reaction mixture was stirred at 45° C. for fifteen minutes, and was then diluted by dropwise addition of 24.5 g. (0.35 mole) of methyl vinyl ketone. The reaction mixture was heated at reflux for three hours following complete addition, and then it was cooled to about 30° C. and added to 500 g. of ice. The aqueous reaction mixture was extracted several times with 50% diethyl ether in ethyl acetate, and the extracts were combined, washed with water, with 10% aqueous sodium hydroxide, again with water and then dried. Removal of the solvent by evaporation under reduced pressure afforded a solid which, following crystallization from ethyl acetate, was identified as 46.1 g. of 9-carbamoyl-9-(3-oxobutyl)fluorene. m.p. 125°–128° C.

Analysis calculated for $C_{18}H_{17}NO_2$; Theory: C, 77.40; H, 6.13; N, 5.01, Found: C, 77.29; H, 6.30; N, 4.96.

Mass spec. M+279.

NMR(CDCl$_3$): δ1.8–2.1 (m, 2H); 1.88 (s, 3H); 2.6–2.95 (m, 2H); 5.0–5.8 (broad doublet, 1H); 7.3–8.0 (m, 8H).

IR(KBr): 1720 cm$^{-1}$, 1660 cm$^{-1}$.

EXAMPLE 3

9-Carbamoyl-9-(3-ethylaminobutyl)fluorene

A solution of 8.5 g. of 9-carbamoyl 9-(3-oxobutyl)-fluorene from Example 2 in 400 ml of ethanol containing 5.0 g. of 5% polladium on carbon and 35 ml. of ethylamine was stirred at 150° C. for eight hours under 1000 psi of hydrogen. The reaction mixture was cooled, filtered and concentrated to dryness. The product was dissolved in 100 ml. of ethyl acetate and 100 ml. of diethyl ether and the solution was extracted several times with 6N hydrochloric acid. The acidic extracts were combined, cooled in an ice bath and made alkaline by addition of 10% sodium hydroxide. The alkaline solution was extracted with fresh ethyl acetate and diethyl ether. The organic layer was washed with water, dried and concentrated to dryness to provide 8.2 g. of the title product. The product was chromatographed over silica gel (eluting with 1% diethylamine in methanol v/v). The chromatographed product was dissolved in diethyl ether and the solution was stirred during addition of hydrogen chloride. The precipitated crystals were collected by filtration and recrystallized from ethanol and ethyl acetate to afford 5.1 g. of 9-carbamoyl-9-(3-ethylaminobutyl)fluorene hydrochloride. m.p. 180°–182° C.

Analysis calc. for $C_{20}H_{25}N_2OCl$; Theory: C, 69.65; H, 7.31; N, 8.12. Found: C, 69.81; H, 7.57; N, 7.90.

EXAMPLE 4

9-Carbamoyl-9-(3-isopropylaminobutyl)fluorene

A solution of 2.35 g. of 9-carbamoyl-9-(3-oxobutyl)-fluorene from Example 2 in 200 ml. of ethanol containing 59.0 g. of isopropylamine and 2.0 g. of 5% palladium on charcoal was stirred for sixteen hours at 25° C. under 60 psi of hydrogen. The reaction mixture was filtered and the filtrate was concentrated to a volume of about 50 ml. The mixture was added to 200 ml. of diethyl ether and extracted with 6N hydrochloric acid. The aqueous acid extract was cooled, made alkaline by addition of 10% aqueous sodium hydroxide, and the alkaline solution was extracted several times with diethyl ether. The ethereal extracts were combined, washed with water, dried and the solvent was removed by evaporation under reduced pressure to provide a solid. The solid was dissolved in fresh diethyl ether and hydrogen chloride was bubbled into the solution. The precipitated crystals which formed were collected by filtration, dried and identified as 829 mg. of 9-carbamoyl-9-(3-isopropylaminobutyl)fluorene hydrochloride. m.p. 204°–206° C.

Analysis calc. for $C_{21}H_{27}N_2OCl$; Theory: C, 70.28; H, 7.58; N, 7.81. Found: C, 70.01; H, 7.69; N, 7.97.

EXAMPLE 5

9-Cyano-9-(3-dimethylaminobutyl)fluorene

To a stirred solution of 3.9 g. of sodium amide in 500 ml. of dry toluene were added 19.1 g. of 9-cyanofluorene. The reaction mixture was stirred at reflux for one hour and then diluted by the dropwise addition of a solution of 18.9 g. of 2-dimethylaminobutyl chloride in 500 ml. of dry toluene. The reaction mixture was heated at reflux for sixteen hours and then diluted by slow addition of 150 ml. of water. The reaction mixture was added to 200 g. of ice, and the aqueous mixture was extracted several times with diethyl ether. The ethereal extracts were combined, washed with water, dried and concentrated to an oil. The oil was distilled to provide 17.4 g. of 9-cyano-9-(3-dimethylaminobutyl)fluorene. b.p. 180°–190° C. @ 0.06 torr

EXAMPLE 6

9-Carbamoyl-9-(3-dimethylaminobutyl)fluorene

A mixture of 10.0 g of 9-cyano-9-(3-dimethylaminobutyl)fluorene from Example 5 and 18.0 g. of concentrated sulfuric acid containing 2.0 g. of water was heated at 95° C. for sixty minutes. The mixture was added to 200 g. of ice and made alkaline by addition of 50% sodium hydroxide. The alkaline solution was extracted several times with 50% diethyl ether-ethyl acetate. The organic extracts were combined, washed with water, dried and concentrated to an oil. The oil was crystallized from petroleum ether to afford 1.7 g. of 9-carbamoyl-9-(3-dimethylaminobutyl)fluorene. m.p. 104°–106° C.

Analysis calc. for $C_{19}H_{24}N_2O$; Theory: C, 77.89; H, 7.84; N, 9.08. Found: C, 77.86; H, 7.74; N, 9.01.

EXAMPLE 7

9-Carbamoyl-9-(3-oxopentyl)fluorene

A solution of 52.3 g. of 9-carbamoylfluorene and 10 ml. of benzyltriethylammonium hydroxide in 700 ml. of tetrahydrofuran was heated at 45° C. for thirty minutes and then cooled to 25° C. The reaction mixture was diluted by addition in one portion of 25.2 g. of ethyl vinyl ketone. The reaction mixture was stirred at 25° C. for sixteen hours and at reflux for three hours. The mixture was cooled, added to 200 g. of ice and extracted with 50% ethyl acetate-diethyl ether. The organic extract was washed with water, with 10% sodium hydroxide, dried and the solvent was removed by evaporation under reduced pressure. The solid residue was crystallized from ethyl acetate and petroleum ether to afford 42.6 g of 9-carbamoyl-9-(3-oxopentyl)fluorene. m.p. 133°–135° C.

Analysis calc. for $C_{18}H_{19}NO_2$; Theory: C, 77.79; H. 6.53; N, 4.77. Found: C, 77.69; H, 6.70; N, 4.66.

EXAMPLE 8

9-Carbamoyl-9-(3-isopropylaminopentyl)fluorene

A mixture of 14.6 g. of 9-carbamoyl-9-(3-oxopentyl)-fluorene from Example 7 and 14.8 g. of isopropylamine in 100 ml. of methanol containing 3.7 g. of 5% palladium on charcoal was heated at 80° C. for eight hours at 750 psi hydrogen. The reaction mixture was cooled, filtered and concentrated to a volume of about 25 ml. The product was added to ethyl acetate and diethyl ether. The organic solution was extracted with 6N hydrochloric acid. The acidic extracts were combined, cooled in ice and made alkaline by addition of 10% sodium hydroxide. The alkaline solution was extracted several times with 50% ethyl acetate in diethyl ether. The extracts were combined, washed with water, dried and concentrated to dryness to provide 4.0 g. of the title compound. The product was dissolved in 50 ml. of ethyl acetate and stirred while 1.38 g. of maleic acid were added. The precipitated solid was collected by filtration and dried to afford 4.0 g. of 9-carbamoyl-9-(3-isopropylaminopentyl)fluorene maleate. m.p. 161°–163° C.

Analysis calc. for $C_{26}H_{32}N_2O_5$; Theory: C, 69.01; H, 7.13; N, 6.19. Found: C, 68.74; H, 7.05; N, 6.32.

EXAMPLE 9

9-Carbamoyl-9-(3-methylaminobutyl)fluorene

A solution of 8.5 g. of 9-carbamoyl-9-(3-oxobutyl)-fluorene in 400 ml. of ethanol containing 35 ml. of methylamine and 5 g. of 5% palladium-on-carbon was stirred at 150° C. for eight hours under 1000 psi of hydrogen. The reaction mixture was cooled, filtered and concentrated to about 50 ml. The solution was added to 200 ml. of 50% ethyl acetate-diethyl ether. The organic solution was washed with water and extracted several times with 6N hydrochloric acid. The acidic extracts were combined, made alkaline by addition of 10% sodium hydroxide, and the alkaline solution was extracted with fresh ethyl acetate/diethyl ether. The organic extracts were combined, washed with water, dried and the solvent was removed to give 4.8 g. of 9-carbamoyl-9-(3-methylaminobutyl)fluorene. The product was combined with 0.557 g. of maleic acid and the mixture was dissolved in warm ethyl acetate. The precipitated solid was collected by filtration, dried and identified as 1.1 g. of 9-carbamoyl-9-(3-methylaminobutyl)fluorene maleate. m.p. 178°–180° C.

Analysis calc. for $C_{23}H_{26}N_2O_5$; Theory: C, 67.30; H, 6.38; N, 6.82. Found: C, 67.04; H, 6.24; N, 6.56.

We claim:
1. A compound of the formula

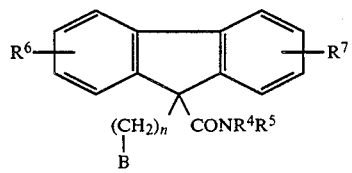

wherein:
$R^4$ and $R^5$ independently are hydrogen or $C_1$–$C_6$ alkyl;
B is

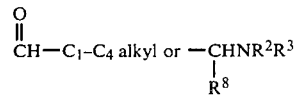

in which $R^2$ and $R^3$ independently are hydrogen, $C_1$–$C_2$ alkyl or

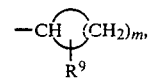

$R^8$ and $R^9$ independently are hydrogen or $C_1$–$C_4$ alkyl;
m and n independently are 2, 3, 4 or 5;
$R^6$ and $R^7$ independently are hydrogen, $C_1$–$C_4$ alkyl or halogen;
provided that $R^8$ is $C_1$–$C_4$ alkyl when both of $R^2$ and $R^3$ are other than

and the pharmaceutically acceptable salts thereof.

2. The compound of claim 1 wherein B is

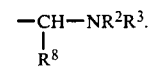

3. The compound of claim 2 wherein $R^3$ is methyl.
4. The compound of claim 2 wherein $R^3$ is ethyl.
5. The compound of claim 2 wherein $R^3$ is cyclopropyl.
6. The compound of claim 2 wherein $R^4$ and $R^5$ both are hydrogen.
7. The compound of claim 6 wherein $R^6$ and $R^7$ both are hydrogen.
8. The compound of claim 7 wherein $R^3$ is $C_1$–$C_2$ alkyl or $C_3$–$C_6$ cycloalkyl.
9. The compound of claim 8, wherein $R^3$ is cyclopropyl.
10. The compound of claim 9, said compound being 9-(3-cyclopropylaminopropyl)-9-aminocarbonylfluorene.
11. The compound of claim 1 as a pharmaceutically acceptable acid addition salt.
12. The compound of claim 11, said compound being 9-(3-cyclopropylaminopropyl)-9-aminocarbonylfluorene hydrochloride.
13. A pharmaceutical formulation which comprises a carrier or diluent admixed with a fluorene antiarrhythmic agent of claim 1.
14. The formulation of claim 13 wherein $R^3$ is $C_1$–$C_2$ alkyl or $C_3$–$C_6$ cycloalkyl.
15. The formulation of claim 14 wherein $R^3$ is cyclopropyl.

* * * * *